(12) United States Patent
Park et al.

(10) Patent No.: US 11,696,709 B2
(45) Date of Patent: Jul. 11, 2023

(54) LIQUID INFORMATION SENSOR AND METHOD OF DRIVING THE SAME

(71) Applicant: UNIVERSITY-INDUSTRY FOUNDATION (UIF), YONSEI UNIVERSITY, Seoul (KR)

(72) Inventors: Cheolmin Park, Seoul (KR); Jong Sung Kim, Seoul (KR); Eui Hyuk Kim, Seoul (KR); Chanho Park, Gyeonggi-do (KR)

(73) Assignee: UNIVERSITY-INDUSTRY FOUNDATION (UIF), YONSEI UNIVERSITY, Seoul (KR)

( * ) Notice: Subject to any disclaimer, the term of this patent is extended or adjusted under 35 U.S.C. 154(b) by 722 days.

(21) Appl. No.: 16/702,766

(22) Filed: Dec. 4, 2019

(65) Prior Publication Data

US 2021/0093232 A1 Apr. 1, 2021

(30) Foreign Application Priority Data

Sep. 30, 2019 (KR) .................. 10-2019-0120703

(51) Int. Cl.
*A61B 5/1468* (2006.01)
*G01N 29/24* (2006.01)
*G01N 29/028* (2006.01)
*A61B 5/00* (2006.01)

(52) U.S. Cl.
CPC .......... *A61B 5/1468* (2013.01); *A61B 5/7415* (2013.01); *G01N 29/028* (2013.01); *G01N 29/2437* (2013.01)

(58) Field of Classification Search
CPC .. A61B 5/1468; A61B 5/7415; G01N 29/028; G01N 29/2437

USPC ......................................................... 600/345
See application file for complete search history.

(56) References Cited

U.S. PATENT DOCUMENTS

| | | | | |
|---|---|---|---|---|
| 9,080,942 | B2* | 7/2015 | Zhong | ................. G01N 27/127 |
| 2003/0076743 | A1* | 4/2003 | Thompson | ............... H04R 1/00 |
| | | | | 367/140 |
| 2016/0172577 | A1* | 6/2016 | Hong | .................... H01L 41/331 |
| | | | | 427/469 |
| 2018/0331278 | A1* | 11/2018 | Hong | .................. H01L 41/0471 |

(Continued)

FOREIGN PATENT DOCUMENTS

| | | | |
|---|---|---|---|
| CN | 1693363 A | * | 11/2005 |
| CN | 112305042 A | * | 2/2021 |
| JP | 2006003267 A | * | 1/2006 |

OTHER PUBLICATIONS

Translation JP-2006003267 (Year: 2016).*

(Continued)

*Primary Examiner* — Alexander A Mercado
*Assistant Examiner* — Monica S Young

(57) ABSTRACT

The present invention relates to a liquid information sensor comprises at least more than one electrode set including a first electrode, and a second electrode which is disposed spaced apart from the first electrode and to which an alternating current signal is applied between the first electrode and the second electrode; and a ferroelectric layer including a first side in contact with the first electrode and the second electrode and a second side facing the first side and defining a receiving area for receiving the target liquid, and generating sound waves by physical vibration when the AC signal is applied.

18 Claims, 10 Drawing Sheets

(56) References Cited

U.S. PATENT DOCUMENTS

2019/0170631 A1* 6/2019 Shachar ............... G01N 29/022
2020/0232897 A1* 7/2020 Hong ................. G01N 29/2437

OTHER PUBLICATIONS

Translation CN-112305042 (Year: 2021).*
Translation CN 1693363 (Year: 2005).*
Kim, J.S., Kim, E.H., Park, C. et al. Sensing and memorising liquids with polarity-interactive ferroelectric sound. Nat Commun 10, 3575 (2019). https://doi.org/10.1038/s41467-019-11478-1 (Year: 2019).*

* cited by examiner

LIQUID INFORMATION SENSOR AND METHOD OF DRIVING THE SAME

CROSS-REFERENCE TO RELATED APPLICATION

This application claims priority of Korean Patent Application No. 10-2019-0120703, filed on Sep. 30, 2019, in the KIPO (Korean Intellectual Property Office), the disclosure of which is incorporated herein entirely by reference.

BACKGROUND OF THE INVENTION

Field of the Invention

The present invention relates to a sensor technology, and more particularly, to a liquid information sensor and a driving method thereof.

Description of the Related Art

The liquid information sensors have been studied in various fields for performing biomedical diagnostics or detecting the toxic liquid substances in a biotechnology field. As a method of obtaining information of a target liquid, there is a method of measuring an electrical signal or detecting a change in resonance frequency according to an impedance. However, the methods using the impedance or resonance frequency have difficulties in configuring additional signal operating processes and/or circuits. As another approach for obtaining information of the target liquid, a method of visually distinguishing using solvatochromism of the target liquid is also being studied. However, there is a need for measuring equipment for measuring the solvatochromism, in which case there is a disadvantage that solubility and portability are reduced due to the weight or volume of the measuring equipment. In order to implement a biotechnology field, for example, a sensor for diagnosing a human body, it is preferable to that sufficient flexibility must be secured to be inserted into or attached to a human body, and the sensor has a simple structure and is miniaturized so that it can be inserted into the human body.

In addition, when the target liquid has a volatility property, the measurement time is limited because it is vaporized and disappeared in the air within a short time. In particular, in the biotechnology field, since the measurement can be performed using only a small amount of the liquid sample, the measurement reliability and accuracy can be deteriorated when the target liquid is vaporized.

SUMMARY OF THE INVENTION

The technological object of the present invention is to provide a liquid information sensor, which can be easily changed due to its flexibility or elasticity, can be attached to a human body or inserted inside the human body because its compact structure allows it to be miniaturized, and can perform very reliable and accurate measurement without the limitation of measurement time even when the target liquid is volatile.

The technological object of the present invention is to provide a method of driving a liquid information sensor having the aforementioned advantages.

A liquid information sensor according to an embodiment of the present invention for solving the above problems is a liquid information sensor for collecting information of the target liquid, and comprises at least more than one electrode set including a first electrode, and a second electrode which is disposed spaced apart from the first electrode and to which an alternating current signal is applied between the first electrode and the second electrode; and a ferroelectric layer including a first side and a second side facing each other, wherein the first electrode and the second electrode are formed on the first side, a receiving region for receiving the target liquid is defined on the second side, and sound waves are generated by physical vibration when the AC signal is applied. Furthermore, it is possible to collect information of the target liquid from a change in intensity of the sound wave that varies according to the polarity of the target liquid.

In one embodiment, the intensity of the sound wave can increase as the polarity of the target liquid increases. In another embodiment, the intensity of the sound wave can be linearly proportional to the relative dielectric constant of the target liquid. In another embodiment, the frequency of the AC signal can be in the range of 20 Hz to 20 kHz.

In one embodiment, the intensity of the sound wave can increase as the frequency of the AC signal increases. In another embodiment, the ferroelectric layer can be PVDF, P(VDF-TrFE), P(VDF-CTFE), P(VDF-CFE), P(VDFHFP), P(VDF-TrFE-CTFE), P(VDF-TrFE-CFE), P(VDF-TrFE-HFP), or a combination thereof.

A liquid information sensor according to an embodiment can be disposed between the first electrode and the second electrode and the first side of the ferroelectric layer, and can further include a protection layer to prevent a short circuit generated due to a ferroelectric layer between the first electrode and the second electrode when the AC signal is applied. In another embodiment, the protection layer can be a conductive polymer. A liquid information sensor according to an embodiment of the present invention can further include a microphone for measuring the intensity of the sound wave. In another embodiment, the liquid information sensor can further include a cover formed on the ferroelectric layer to prevent vaporization of the target liquid.

In one embodiment, the electrode set can be a plurality of electrode sets arranged in an array type. In another embodiment, the liquid information sensor can be a tubular sensor formed by rolling a laminate of the electrode set and the ferroelectric layer. In yet another embodiment, the radius of curvature of the tubular sensor can be in the range of 1 mm to 100 mm. In another embodiment, the electrode set can be a plurality of electrode sets spaced apart by a predetermined distance.

A method of driving a liquid information sensor according to another embodiment of the present invention for solving the above problems is a method of driving a liquid information sensor for collecting information of a target liquid. The liquid information sensor can comprise at least more than one electrode set including a first electrode, and a second electrode which is disposed spaced apart from the first electrode and to which an alternating current signal is applied between the first electrode and the second electrode; and a ferroelectric layer including a first side in contact with the first electrode and the second electrode and a second side facing the first side and defining a receiving area for receiving the target liquid, and generating sound waves by physical vibration when the AC signal is applied. Furthermore, the method can comprise a step for providing a target liquid to the receiving region, a step for generating a sound wave by applying an alternating current signal between a first electrode and a second electrode, and a step for measuring an intensity of the sound wave that varies according to the polarity of the target liquid.

In the method of driving a liquid information sensor according to an embodiment, the target liquid can be continuously provided, and the intensity of the sound wave can be measured according to in-situ method.

A method of driving a liquid information sensor according to a yet another embodiment of the present invention for solving the above problems is a method of driving a liquid information sensor for collecting information of a target liquid. The liquid information sensor can comprise at least more than one electrode set including a first electrode, and a second electrode which is disposed spaced apart from the first electrode and to which an alternating current signal is applied between the first electrode and the second electrode; and a ferroelectric layer including a receiving region in contact with the electrode set on one side thereof and receiving the target liquid on the other side facing the one side, and generating sound waves by physical vibration when the AC signal is applied. The method can comprise a writing step for providing the target liquid on the receiving region and for applying a direct current signal between the first electrode and the second electrode to generate polarization in the ferroelectric layer; a reading step for replacing the target liquid with a conductive material and for generating sound waves by applying an alternating current signal between the first electrode and the second electrode; and an erasing step for removing the polarization by applying a direct current signal having a polarity opposite to that of the direct current signal between the first electrode and the second electrode. In one embodiment, the magnitude of the DC signal can be in the range of 0.5 kV to 5 kV.

A liquid information sensor according to an embodiment of the present invention includes a ferroelectric layer comprising the first electrode and the second electrode spaced apart from each other; and a receiving region in contact with the first electrode and the second electrode on one side and receiving target liquid on the other side facing the one side. Therefore, it is possible to miniaturize by a simple structure so that the available range can be wide, and portability can be improved remarkably.

Furthermore, in the liquid information sensor, a sound wave which can be generated due to the physical vibration when the AC signal is applied, and whose intensity varies depending on the polarity of the target liquid can be measured. Therefore, it is possible to obtain information of the target liquid by measuring the sound waves propagated in all directions without physically contacting the target liquid or the ferroelectric layer.

The method of driving the liquid information sensor according to another exemplary embodiment of the present invention has the above-described advantages, and the polarity of the ferroelectric layer is maintained for a predetermined time even if the target liquid is partially volatilized due to the residual polarization characteristic of the ferroelectric layer. Therefore, the limitation of measurement time can be relaxed, the reliability and accuracy of the liquid information sensor can be improved, and a sensor having a memory function capable of storing sensing information for a predetermined time can be implemented

BRIEF DESCRIPTION OF THE DRAWINGS

The above and other features and advantages will become more apparent to those of ordinary skill in the art by describing in detail exemplary embodiments with reference to the attached drawings, in which.

In the following description, the same or similar elements are labeled with the same or similar reference numbers.

DETAILED DESCRIPTION

Figure 1:
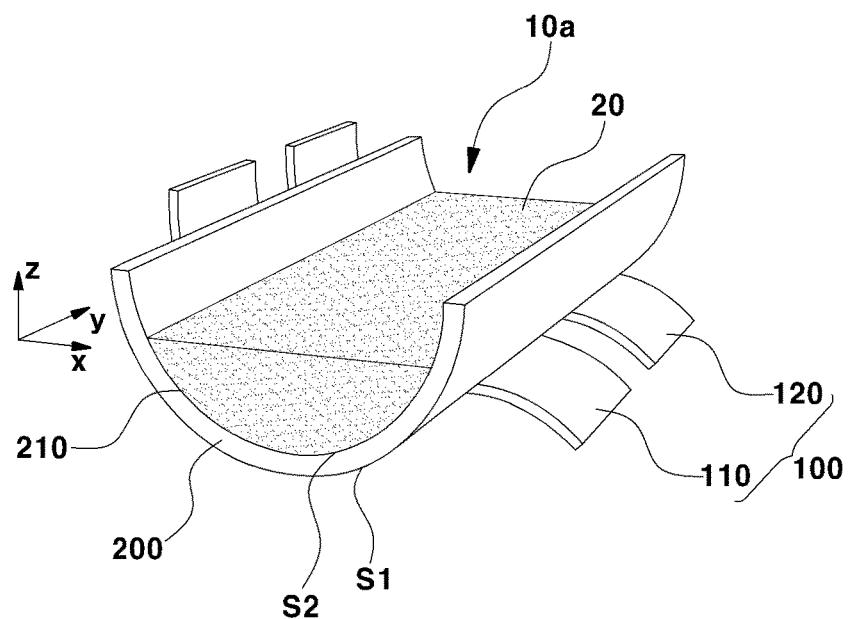
FIG. 1 is a perspective view of a liquid information sensor according to an embodiment of the present invention.

The present invention now will be described more fully hereinafter with reference to the accompanying drawings, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "includes", "comprises" and/or "comprising," when used in this specification, specify the presence of stated features, integers, steps, operations, elements, and/or components, but do not preclude the presence or addition of one or more other features, integers, steps, operations, elements, components, and/or groups thereof. In addition, a term such as a "unit", a "module", a "block" or like, when used in the specification, represents a unit that processes at least one function or operation, and the unit or the like may be implemented by hardware or software or a combination of hardware and software.

Reference herein to a layer formed "on" a substrate or other layer refers to a layer formed directly on top of the substrate or other layer or to an intermediate layer or intermediate layers formed on the substrate or other layer. It will also be understood by those skilled in the art that structures or shapes that are "adjacent" to other structures or shapes may have portions that overlap or are disposed below the adjacent features.

In this specification, the relative terms, such as "below", "above", "upper", "lower", "horizontal", and "vertical", may be used to describe the relationship of one component, layer, or region to another component, layer, or region, as shown in the accompanying drawings. It is to be understood that these terms are intended to encompass not only the directions indicated in the figures, but also the other directions of the elements.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Preferred embodiments will now be described more fully hereinafter with reference to the accompanying drawings. However, they may be embodied in different forms and should not be construed as limited to the embodiments set forth herein. Rather, these embodiments are provided so that this disclosure will be thorough and complete, and will fully convey the scope of the disclosure to those skilled in the art.

FIG. 1 is a perspective view of a liquid information sensor 10a according to an embodiment of the present invention.

Referring to FIG. 1, in one embodiment, the liquid information sensor 10a can include an electrode set 100 including a first electrode 110 and a second electrode 120, and a ferroelectric layer 200 having a first side S1 and a second side S2 facing each other. The first electrode 110 and the second electrode 120 can be disposed on the first side S1 of the ferroelectric layer 200. The first electrode 110 and the second electrode 120 can be disposed on the first side S1 of the ferroelectric layer 200.

The first electrode 110 and the second electrode 110 of the electrode set 100 can be spaced apart from each other, and an AC signal can be applied between the first electrode 110 and the second electrode 120. One or more electrode sets 100 can be provided. In addition, each of the first electrode 110 and the second electrode 120 constituting one electrode set 100 can have at least one or more sub-electrodes, to each of which a common current or voltage signal can be applied. Description of the plurality of electrode sets 100 will be described later with reference to FIG. 5A.

In one embodiment, when there are a plurality of electrode sets 100, each of the plurality of electrode sets 100 can be spaced apart from each other. In another embodiment, the neighboring electrode sets 100 among the plurality of electrode sets 100 can share one electrode. For example, the second electrode 120 of any electrode set 100 of the plurality of electrode sets 100 can be the first electrode of the electrode set 100 adjacent to the any electrode set 100. Alternatively, the second electrode 120 of any electrode set 100 and the first electrode 110 of the electrode set 100 adjacent to any electrode set 100 can be integrated.

In one embodiment, the first electrode 110 and/or the second electrode 120 can comprise a conductive polymer. The conductive polymer can be PEDOT:PSS (Poly(3,4-ethylenedioxythiophene)poly(styrenesulfonate), poly(3,4-ethylene dioxythiophene)poly(styrenesulfonate)). In another embodiment, the conductive polymer can be polyacetylene, polypyrrole, polyaniline, poly(p-phenylene vinylene), poly(thiophene) poly(3,4-ethylenedioxythiophene)) or a combination thereof. According to an embodiment of the present invention, the first electrode 110 or the second electrode 120 can have flexibility or stretchability so that the liquid information sensor 10a is not limited to the shape of the first electrode 110 or the second electrode 120. Therefore, there is an advantage that various types of liquid information sensors 10 can be implemented by modifying the shape of the electrodes. In other embodiments, the ferroelectric layer 200 can comprise a transparent ferroelectric material.

In one embodiment, the first electrode 110 and/or the second electrode 120 can be a flat plate having an aspect ratio of 1 or more, and in this case, the long direction of the horizontal direction or the vertical direction can be defined as the longitudinal direction. The flat plate can be in the form of a strip but is not limited thereto. The flat plate can have a polygonal shape such as a circle, a square, a pentagon, a hexagon, or a combination thereof, or a shape having a bend portion such as a meander or a wave shape. In another embodiment, the first electrode 110 and/or the second electrode 120 can be formed in a dot shape, and in this case, a plurality of electrode sets 100 composed of the first electrode 110 and the second electrode 120 can be arranged in an array type. In another embodiment, the first electrode 110 and/or the second electrode 120 can have a ring shape curved in the longitudinal direction or a ring shape in which a portion thereof is cut off. The foregoing shapes are the non-limiting examples and they do not limit the shapes of the first electrode 110 and/or the second electrode 120.

In one embodiment, the receiving region 210 for receiving the target liquid 20 can be defined on the second side S2 of the ferroelectric layer 200. The receiving region 210 can be a recess formed on the second side S2 and suitable for storing a predetermined volume of the target liquid. The recess can be the entire second side S2 of the ferroelectric layer 200 or can be a partial region recessed in the second side S2. The cross section of the recess can be a semi-circle as shown in FIG. 1. As another example, the cross section of the recess can be a rectangular shape, a triangular shape or, a shape having a larger outer circumference larger than that of semicircular arc, or a shape having an outer circumference smaller than that of semicircular arc. The recess can have an extending direction in a first direction (x direction), and the first electrode 110 and the second electrode 120 can extend in a second direction(y) direction different from the first direction. In one embodiment, the first direction (x direction) and the second direction (y direction) can be orthogonal to each other. When the receiving region 210 has a curved side in a direction perpendicular to the first direction (x direction), the first electrode 110 and the second electrode 120 can extend along the curved side. At this time, the first direction (x direction) of the first electrode 110 and the second direction (y direction) of the second electrode 120 can be a direction perpendicular to the first direction (x direction).

In an embodiment, the second side S2 of the ferroelectric layer 200 in which the receiving region 210 is defined is not limited to a curved side as shown in FIG. 1 and can have a flat region. In this case, the first side S1 of the ferroelectric layer 200 can also have a flat area, and the first electrode 110 and the second electrode 120 can be formed on the flat area.

In an embodiment, when an AC signal is applied between the first electrode 110 and the second electrode 120, the ferroelectric layer 200 can physically vibrate. Vibration of the ferroelectric layer 200 can generate sound waves in adjacent media. The ferroelectric layer 200 can generate a piezoelectric effect capable of reversible conversion of electrical energy and mechanical energy. Accordingly, when an AC signal is applied to the ferroelectric layer 200, the electrical energy generated by the AC signal can be converted into mechanical energy due to the piezoelectric effect, and the sound wave can be generated by the mechanical energy. In one embodiment, the intensity of the sound wave can vary depending on the polarity of the target liquid 20 provided in the receiving region 210. The liquid information sensor 10a can collect information about the target liquid 20 from the change in intensity of the sound wave.

In one embodiment, the first electrode 110 and/or the second electrode 120 can be a transparent electrode. For example, the transparent electrode can include a transparent conductive oxide (TCO) such as indium tin oxide (ITO) or antimony tin oxide (ATO). In another embodiment, the transparent electrode can include at least any one of carbon nano tubes (CNT), graphene, or silver nano wires. The foregoing materials are non-limiting examples, and for example, all kinds of electrode materials having a transparency of 70% or more can be used.

Figure 2A:
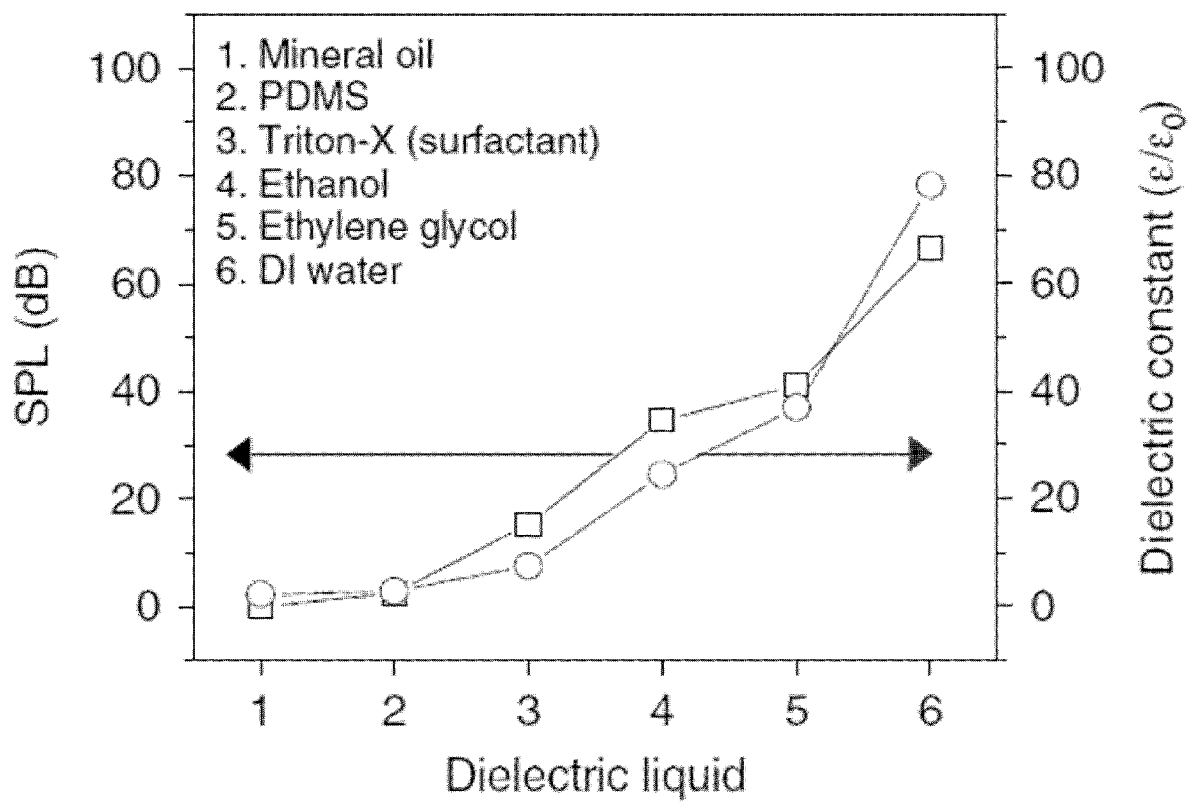
FIG. 2A is a graph measuring the change in intensity of sound waves according to the polarity of the target liquid according to one embodiment of the present invention.
Figure 2B:
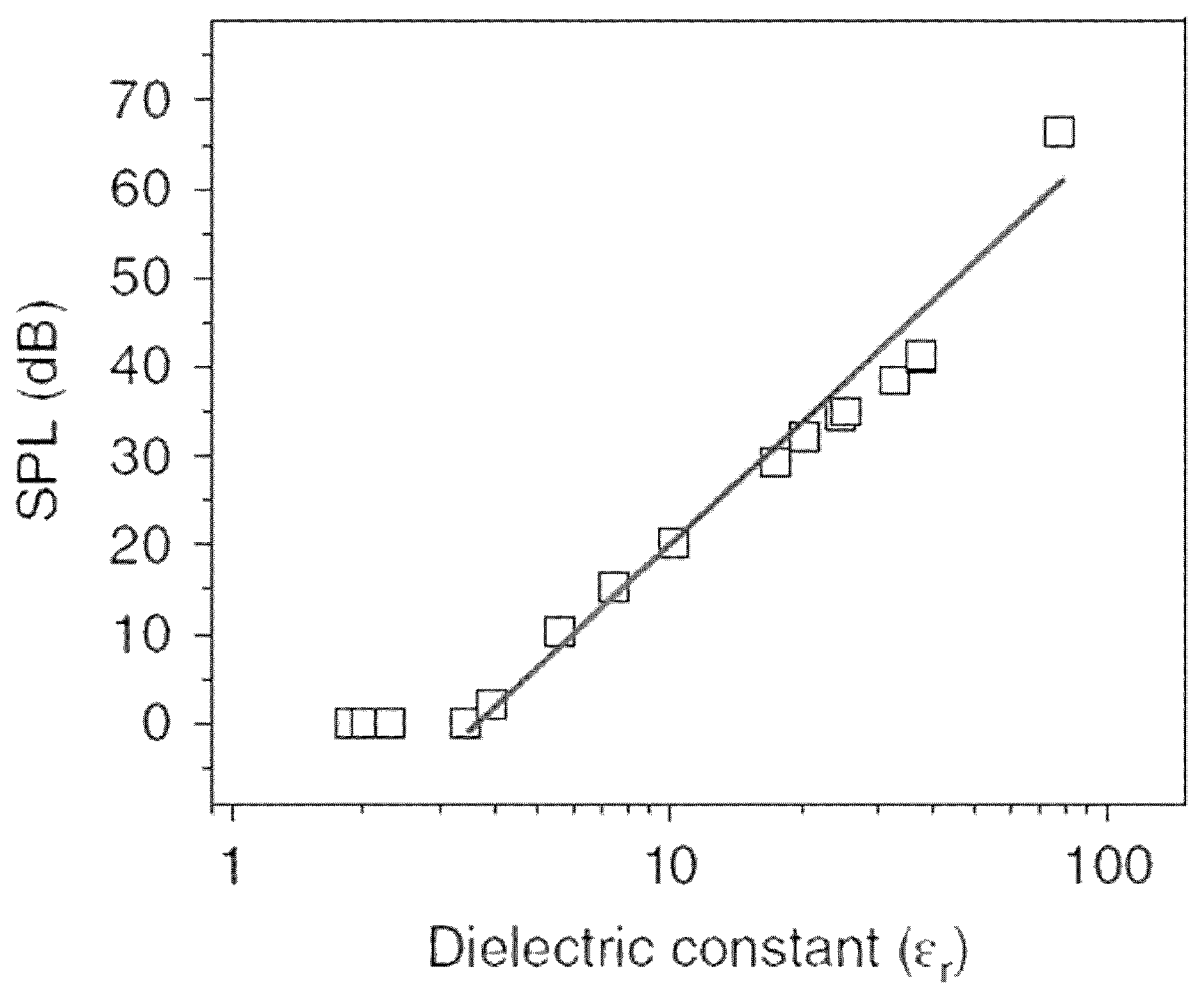
FIG. 2B is a graph measuring the correlation between the relative dielectric constant of the target liquid and the intensity of sound waves.
Figure 2C:
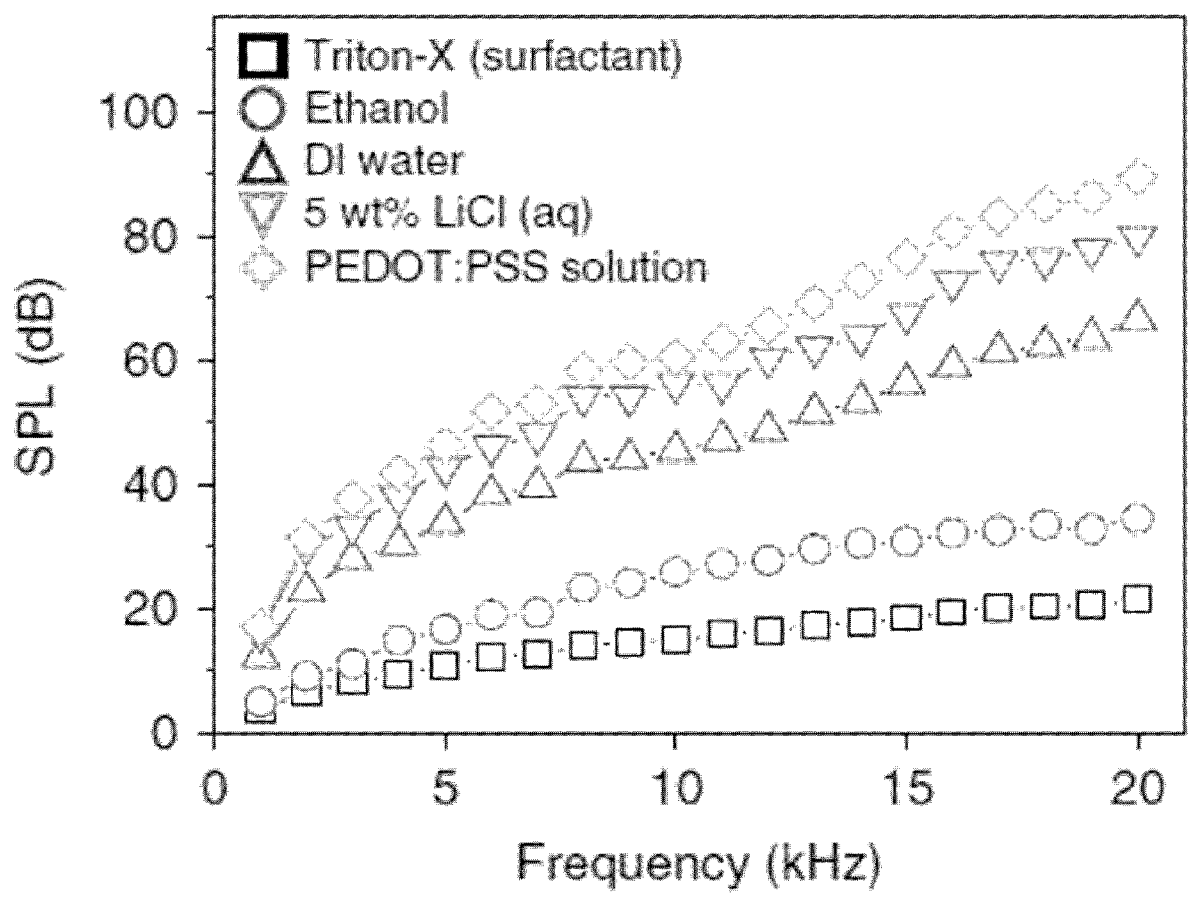
FIG. 2C is a graph measuring the intensity of sound waves according to the frequency of an AC signal.

FIG. 2A is a graph measuring the change in intensity of sound waves according to the polarity of the target liquid 20 according to one embodiment of the present invention. FIG. 2B is a graph measuring the correlation between the relative dielectric constant of the target liquid 20 and the intensity of sound waves, and FIG. 2C is a graph measuring the intensity of sound waves according to the frequency of an AC signal.

Referring to FIG. 2A, in one embodiment, the intensity of the sound wave can increase as the polarity of the target liquid 20 increases. Unit of the intensity of the sound wave can be decibel (dB). In FIG. 2A, as the target liquid 20, for example, mineral oil 1, polydimethylsiloxane (PDMS, 2), triton-X 3, ethanol 4, ethylene glycol 5, distilled water (DI water, 6) were used, but these are non-limiting examples and they do not limit the present invention. The relative dielectric constant of the target liquids 20 is the lowest in mineral oil, and can increase in the order of polydimethylsiloxane, triton-X, ethanol and ethylene glycol and can become the highest in the distilled water. It can be seen that the intensity of sound waves measured by providing each of target liquid 20 is the lowest in mineral oil and the largest in distilled water as the magnitude of the dielectric constant increases. The main reason of it is as follows. As the relative dielectric constant of the target liquid 20 increases, the magnitude of the polarity also increases, and as the magnitude of the polarity increases, the electrical resistance of the target liquid 20 decreases. Accordingly, while the electrical consumption of the target liquid 20 is reduced, much energy is converted into mechanical energy and is used to generate the sound waves.

Referring to FIG. 2B, in one embodiment, the intensity of the sound wave can be linearly proportional to the relative dielectric constant of the target liquid 20. In another embodiment, it is possible to define sensitivity, which is the increase rate of the strength of the sound wave relative to the increase rate of the relative dielectric constant. In this case, a relational expression such as the following Equation 1 can be established between the sound wave intensity and the relative dielectric constant. In Equation 1, SPL can represent the strength of sound waves, $\varepsilon_r$ is a relative dielectric constant, and a can be a sensitivity. The sensitivity can be in the range of 0.7 dB/$\varepsilon_r$ to 0.8 dB/$\varepsilon_r$, for example, 0.75 dB/$\varepsilon_r$.

$$SPL(dB) = \alpha \times \varepsilon_r \quad \text{[Equation 1]}$$

According to an embodiment of the present invention, a library in which the intensity of the sound waves for the various types of target liquids 20 is measured and databased can be provided. In this case, the liquid information sensor 10a can be used to distinguish any kind of colorless or odorless liquid. Alternatively, it is also possible to estimate the type of liquid by measuring the relative dielectric constant of the unknown liquid and using the relational expression as in Equation 1 even if the arbitrary liquid does not exist in the library.

In another embodiment, the intensity of the sound wave can increase as the ion concentration of the target liquid 20 including metal ions or non-metal ions increases. For example, when the concentration of substances such as salts, bases or acids dissolved in the target liquid 20 is changed, as the concentration is getting higher and higher, the conductivity of the target liquid 20 can be higher. As the conductivity is getting higher and higher, the electrical energy consumed in the target liquid 20 is getting smaller and smaller. Therefore, the intensity of sound waves generated can increase.

Referring to FIG. 2C, in one embodiment, the frequency of the AC signal applied between the first electrode 110 and the second electrode 120 can be in the range of 20 Hz to 20 kHz. The frequency range corresponds to the audible frequency range. According to the exemplary embodiment of the present invention, the intensity of the sound wave can be measured by using a microphone 500 within the audible frequency range that is commercially available without expensive equipment for measuring ultrasonic waves or low frequencies. Alternatively, when sound waves within the audible frequency range are generated, the strength of the sound waves can be detected by hearing of the human body without a mechanical device such as the microphone 500.

In another embodiment, the intensity of the sound wave can increase as the frequency of the AC signal increases. This is because the intensity of vibration of the ferroelectric layer 200 increases when the frequency is increased.

In one embodiment, the dependence of the intensity of the sound wave on the frequency can increase as the polarity of the target liquid 20 increases. The polarity of the target liquid 20 can increase in the order of triton-X, ethanol, distilled water, 5 wt % LiCL(aq), and PEDOT:PSS solution. The types of the target liquids 20 described above are non-limiting examples and do not limit the present invention. In addition, it can be seen that the magnitude of the difference in the intensity of the sound wave between the target liquids 20 increases as the frequency increases. For example, it can be seen that the difference in the intensity of the sound waves of Triton-X and PEDOT:PSS aqueous solution is larger in a case that the frequency is 20 kHz, as compared with a case that the frequency is 20 Hz.

Referring to FIG. 1, in one embodiment, the ferroelectric layer 200 can be a polymer having ferroelectricity. Specifically, the ferroelectric layer 200 can include a fluorinated copolymer having a high dielectric constant and having a viscoelastic behavior. For example, the ferroelectric layer 200 can include a PVDF-based polymer including PVDF, P(VDFTrFE), P(VDF-CTFE), P(VDF-CFE), P(VDF-HFP), P (VDF-TrFE-CTFE), P(VDF-TrFE-CFE), PV(VDF-TrFE-HFP) or a combination thereof, but is not limited thereto.

Figure 3:
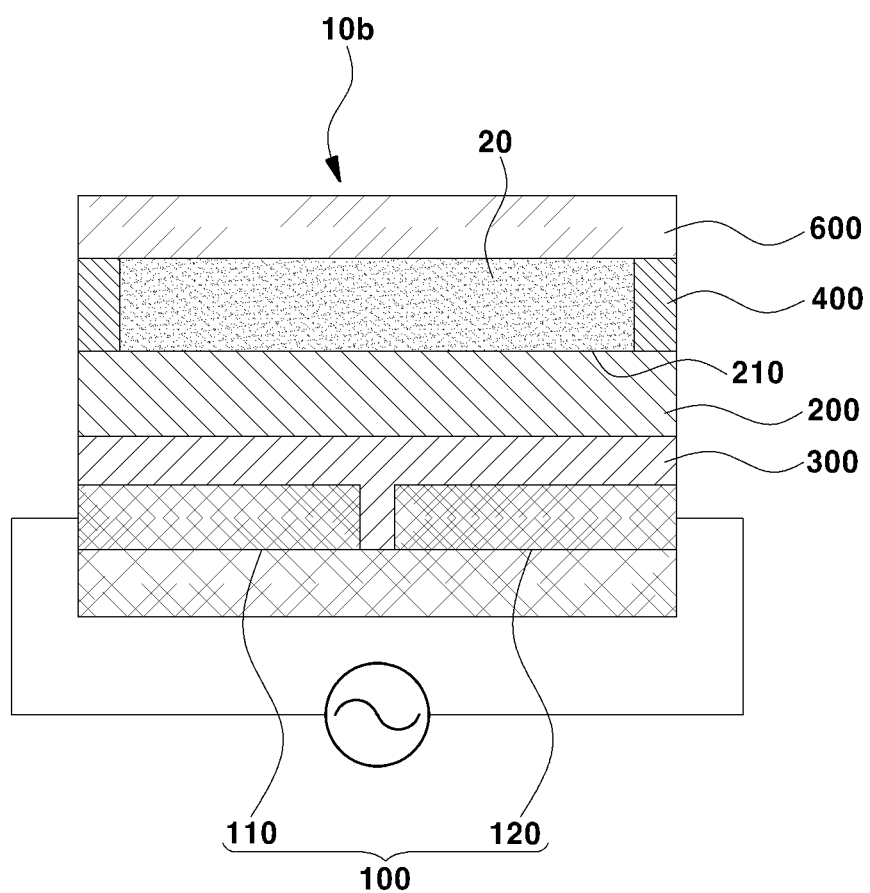
FIG. 3 is a diagram showing a liquid information sensor according to another embodiment of the present invention.

FIG. 3 is a diagram showing a liquid information sensor 10 according to another embodiment of the present invention.

Referring to FIG. 3, in one embodiment, the liquid information sensor 10b can be disposed between the first electrode 110 and the first side S1 of the ferroelectric layer 200, and between the second electrode 120 and the first side S1 of the ferroelectric layer 200. The liquid information sensor 10b can further include a protection layer 300 that prevents a short circuit caused by the ferroelectric layer 200 when AC signal is applied, between the first electrode 110 and the second electrode 120. When a high voltage AC signal is applied, a short circuit can occur between the first electrode 110 and the second electrode 120. When the short circuit occurs, no voltage is applied to the ferroelectric layer 200 and thus, sound waves cannot be generated. The protection layer 300 can be formed around the first electrode 110 and/or the second electrode 120 to prevent the short circuit.

In one embodiment, the protection layer 300 can comprise a conductive polymer. The conductive polymer is poly(N- vinylcarbazole) (PVK), and the insulating polymer is poly methyl methacrylate(PMMA), poly-4-vinyl-phenol(PVP), polyimide(PI) and polystyrene(PS) or a combination thereof. Preferably, poly(methyl methacrylate) (PMMA) can be included. This is a non-limiting example and does not limit the present invention, various known conductive polymers can be applied. According to the exemplary embodiment of the present invention, the conductive polymer can be easily deformed because of elasticity or flexibility provided to it. Therefore, there is an advantage that the liquid information sensor 10 of various shapes can be implemented.

In one embodiment, the thickness of the protection layer 300 can be in the range of 0.5 µm to 3 µm, preferably in the range of 1.0 µm to 2.0 µm. When the thickness is less than 0.5 µm, there is a high possibility that a short circuit between the first electrode 110 and the second electrode 120 can occur. When the thickness exceeds 3 µm, the magnitude of the voltage applied to the protection layer 300 increases, and the magnitude of the voltage applied to the ferroelectric layer 200 decreases, thereby causing unnecessary waste of power. As a result, the intensity difference of the sound waves according to the polarity of the target liquid 20 can be reduced, thereby reducing the accuracy.

In one embodiment, the liquid information sensor 10 can further include a spacer 400 formed on the ferroelectric layer 200 to define the receiving region 210. The thickness of the spacer 400 can be about 1 mm. For example, the spacer 400 can be a tape provided with an adhesive on one side thereof to facilitate attachment to the ferroelectric layer 200. This is only a non-limiting example, and various known materials can be applied. According to the exemplary embodiment of the present invention, the spacer 400 is formed around the receiving region 210 of the target liquid 20, thereby preventing the target liquid 20 from overflowing and it is also possible to increase the volume of acceptable target liquid 20.

In one embodiment, the liquid information sensor 10 can further include a cover 600 to prevent vaporization of the target liquid 20. The cover 600 can be detachable and attachable on the ferroelectric layer 200 to cover the cover 600 after providing the target liquid 20 to the receiving region 210. In another embodiment, a spacer 400 can be provided on the ferroelectric layer 200, and a cover 600 can be attached to the spacer 400.

Figure 4:
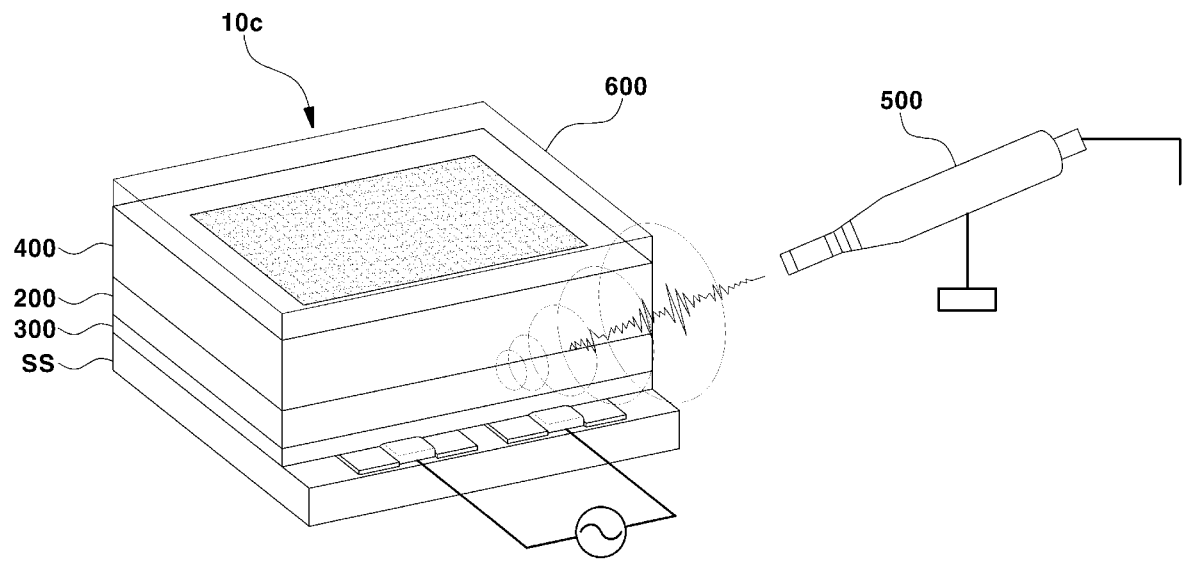
FIG. 4 is a diagram showing the liquid information sensor according to another embodiment of the present invention.

FIG. 4 is a diagram showing the liquid information sensor 10c according to another embodiment of the present invention.

Referring to FIG. 4, in one embodiment, the liquid information sensor 10c can further include a microphone 500. The microphone 500 can be a microphone 500 mounted on a smartphone, a microphone 500 for voice recording, or a microphone 500 for a recorder. For example, the microphone 500 can be an omni-directional microphone 500. This is a non-limiting example and does not limit the invention, and various kinds of known microphones 500 can be used. According to an exemplary embodiment of the present invention, when collecting the information of the target liquid 20, the information of the target liquid 20 can be collected by measuring the intensity of sound waves emitted in all directions without physically contacting the liquid information sensor 10c provided with the target liquid 20 or the target liquid 20.

In one embodiment, the liquid information sensor 10c can further include a substrate SS on which the electrode set 100 and the ferroelectric layer 200 are formed. The substrate SS can include an insulating polymer, and for example, can include polyvinylidene fluoride (PVDF). This is a non-limiting example, and it is possible to apply a variety of known polymers.

Figure 5A:
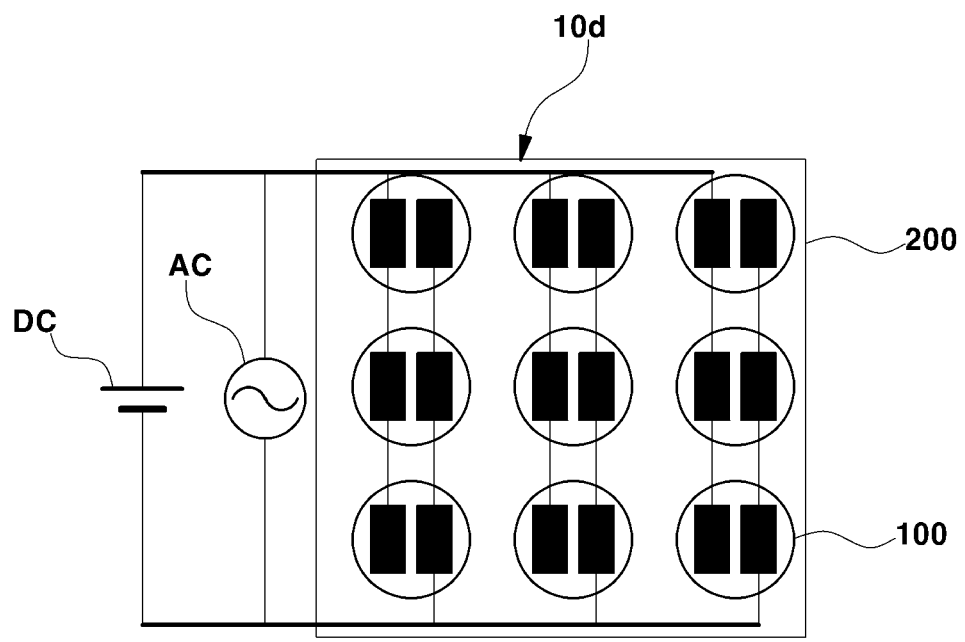
FIG. 5A to FIG. 5C are diagrams illustrating a liquid information sensor according to various embodiments of the present invention.
Figure 5B:
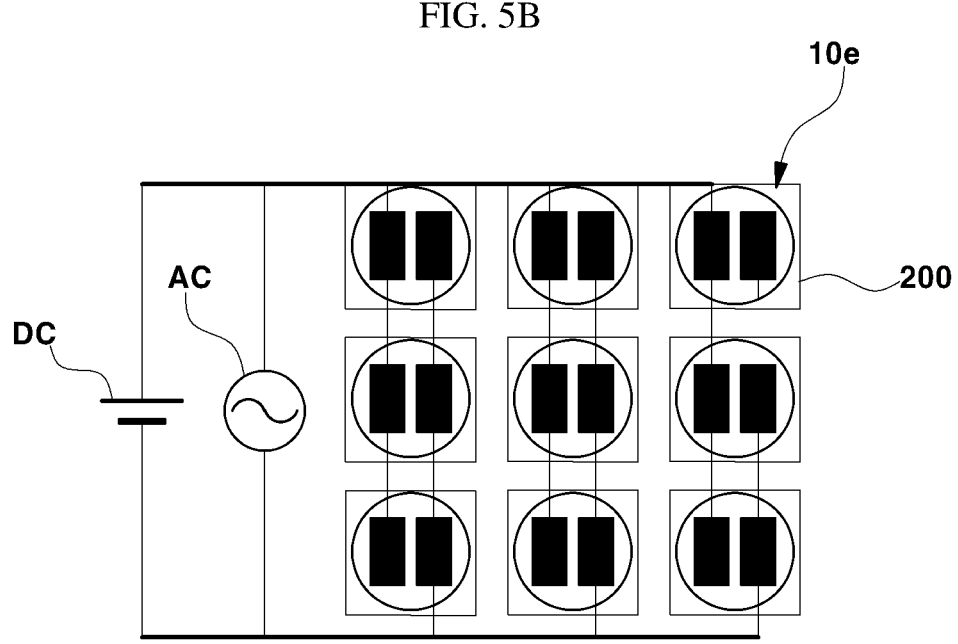
Figure 5C:
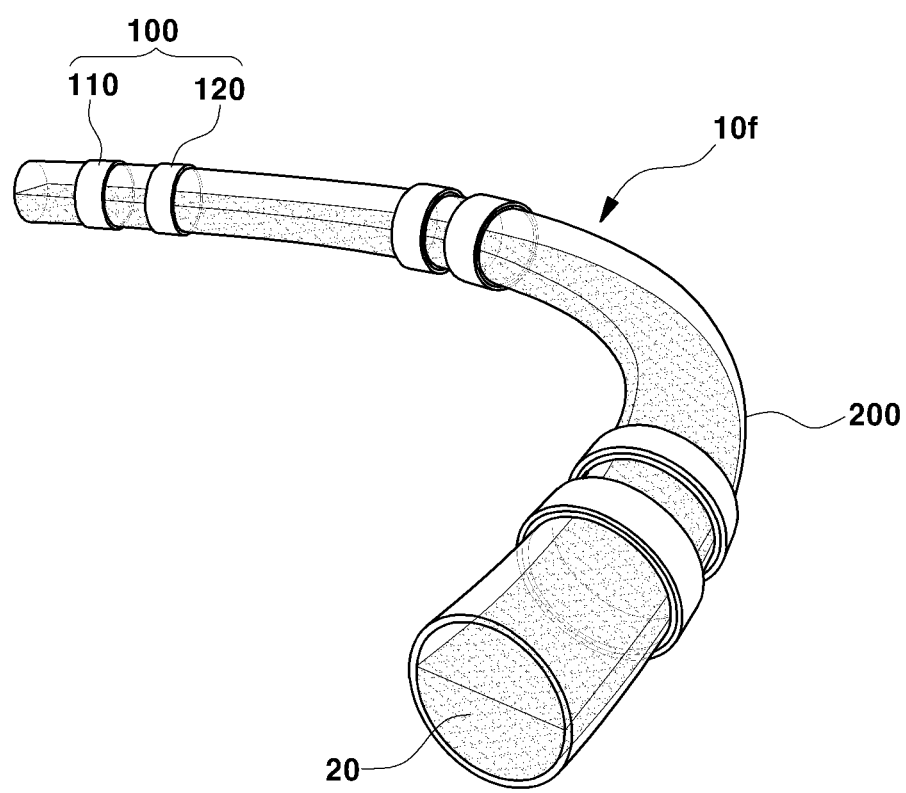

FIG. 5A to FIG. 5C are diagrams illustrating a liquid information sensor 10d according to various embodiments of the present invention.

Referring to FIG. 5A, in one embodiment, the liquid information sensor 10d can comprise the plurality of electrode sets 100 arranged in an array below a single ferroelectric layer 200 or a stack consisting of a single ferroelectric layer 200 and a protection layer 300. For example, the plurality of electrode sets 100 can be electrode sets 100 arranged in an array of 3×3. A plurality of receiving regions 210 can be formed on the ferroelectric layer 200 on each of the plurality of electrode sets 100.

In one embodiment, the plurality of electrode sets 100 are all electrically connected to receive the same direct current signal and/or alternating current signal, or only at least any column or at least any row of the plurality of electrode sets 100 can be electrically connected to receive the same DC signal and/or AC signal.

In an embodiment, DC signals having different magnitudes can be applied to each of the plurality of electrode sets 100 to form different residual polarizations in some regions on each of the electrode sets 100 of the ferroelectric layer 200. For example, the magnitude of the voltage of the DC signals can be in the range of 1.0 kV to 1.4 kV. Thereafter, the target liquid 20 is provided to any one of the pluralities of receiving regions 210 on the plurality of electrode sets 100, and then an AC signal is applied to the plurality of electrode sets 100. In this case, the intensity of sound waves generated according to the position of the target liquid 20 can vary.

According to an embodiment of the present invention, after providing the target liquid 20 at an arbitrary point of the plurality of arrays, the point where the target liquid 20 is provided can be determined by measuring the intensity of sound waves that vary according to the point where the target liquid 20 is provided.

Referring to FIG. 5B, in another embodiment, a plurality of liquid information sensors 10e having one electrode set 100 can be arranged in an array form. The plurality of liquid information sensors 10e can receive the same or different direct current signals and/or alternating current signals. A detailed description of the plurality of liquid information sensors 10e can refer to the disclosures of FIG. 5A if there are no contradictory points.

Referring to FIG. 5C, the liquid information sensor 10f according to an embodiment can be a tubular sensor formed by rolling a laminate of the electrode set 100 and the ferroelectric layer 200. In one embodiment, the target liquid 20 can be provided inside the tubular sensor, and an AC voltage can be applied to the ring-shaped electrode set 100 surrounding the tubular ferroelectric layer 200. In another embodiment, the laminate can be repeatedly rolled two or more times to form a jellyroll.

In one embodiment, the radius of curvature of the tubular sensor can be in the range of 1 mm to 100 mm. It can be understood that the radius of curvature refers to the inverse of the curvature and can mean the radius of a circle having the same curvature as the curvature of the tubular sensor. When the radius of curvature is less than 1 mm, the receiving region 210 of the target liquid 20 is reduced, and a sufficient amount of polarization is not formed in the ferroelectric layer 200, so that the accuracy of the liquid information sensor 10 can be reduced. In addition, when the radius of curvature exceeds 100 mm, the thickness of the tubular sensor is increased, the supply amount of the target liquid 20 can be increased, and the volume of the tubular sensor is increased. As a result of them, the miniaturization of the liquid information sensor 10f can be hindered.

In an embodiment, the electrode set 100 of the liquid information sensor 10f can be a plural type, and the plurality of electrode sets 100 can be disposed to be spaced apart by a predetermined distance in the longitudinal direction of the tubular sensor. When the liquid information sensor 10f according to one embodiment includes a plurality of electrode sets 100, the velocity of the target liquid 20 can be measured as described below.

Figure 6:
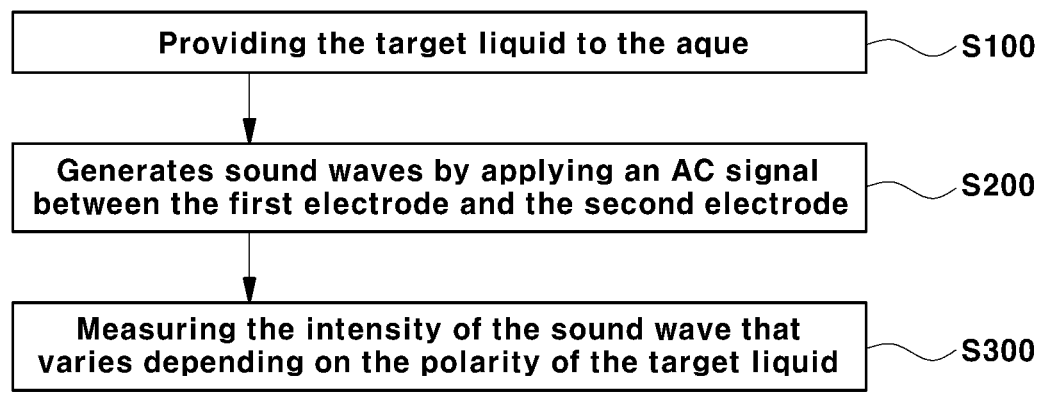
FIG. 6 is a flowchart illustrating a method of driving a liquid information sensor according to an embodiment of the present invention.

FIG. 6 is a flowchart of a method of driving liquid information sensors 10a to 10f according to an embodiment of the present invention.

In one embodiment, the liquid information sensors 10a to 10f can comprise at least more than one electrode set 100 including a first electrode 110, and a second electrode 120 which is disposed spaced apart from the first electrode 110 and to which an AC current signal is applied between the first electrode 110 and the second electrode 120; and a ferroelectric layer 200 including a first side S1 in contact with the first electrode 110 and the second electrode 120 and a second side S2 facing the first side S1 and defining a receiving region for receiving the target liquid, and generating sound waves by physical vibration when the AC signal is applied. In connection with the detailed description of the liquid information sensor 10, the disclosures of the liquid information sensor 10 of FIGS. 1 to 5C can be referred to if there are no inconsistencies.

Referring to FIG. 6, in one embodiment, the target liquid 20 is first provided to the receiving region 210(S100). The target liquid 20 can be deposited on the receiving region 210 using a tool such as a pipette or can be accommodated in the recess when the receiving region 210 is a recess. In other embodiments, the subject liquid 20 can be continuously supplied at a constant flow rate or a variable flow rate.

Next, an AC signal can be applied between the first electrode 110 and the second electrode 120 to generate sound waves(S200). As described above, in one embodiment, the frequency of the AC signal can be in the range of 20 Hz to 20 kHz. The magnitude of the voltage of the AC signal can be 50V to 500V, for example, 70V to 200V, and preferably 100V. The voltage can be set to an appropriate value according to the thickness of the ferroelectric layer 200 or the protection layer 300 and the amount of the target liquid 20.

Next, the intensity of the sound wave that is changed according to the polarity of the target liquid 20 can be measured (S300). The strength of the sound wave can be sensed by hearing ability or measured by a wave graph over time using the microphone 500. The microphone 500 can measure the intensity of the sound wave in physical contact with the liquid detection sensor or measure the intensity of the sound wave in the non-contact state with the liquid detection sensor.

In one embodiment, the object liquid 20 can be provided continuously, and the intensity of the sound wave can be measured according to an in-situ method. While the target liquid 20 is continuously provided, the intensity of sound waves generated by the liquid information sensor 10 can be continuously measured to measure a change in sound waves over time. In another embodiment, when the liquid information sensor 10 includes a plurality of electrode sets 100, while continuously supplying the target liquid 20. The intensity of sound waves that vary according to the number of the electrode set 100 through which the target liquid 20 passes can be measured. For example, the first electrode set 100 and the second electrode set 100 are disposed and first of all, the target liquid 20 continuously supplied passes through the first electrode set 100. Subsequently, while passing through the second electrode set 100, the intensity of a sound wave measured when passing through the first electrode set 100 and the second electrode set 100 together can be greater than that of a sound wave measured when passing through only the first electrode set 100. According to an embodiment of the present invention, when measuring the change in the intensity of the sound wave generated by continuously supplying the target liquid 20 over time, the moving speed of the target liquid 20 can be measured by the time required until the intensity of the sound wave changes.

FIG. 7A to FIG. 7F are diagrams illustrating driving methods of the liquid detection sensors 10a to 10f according to another embodiment.

Figure 7A:
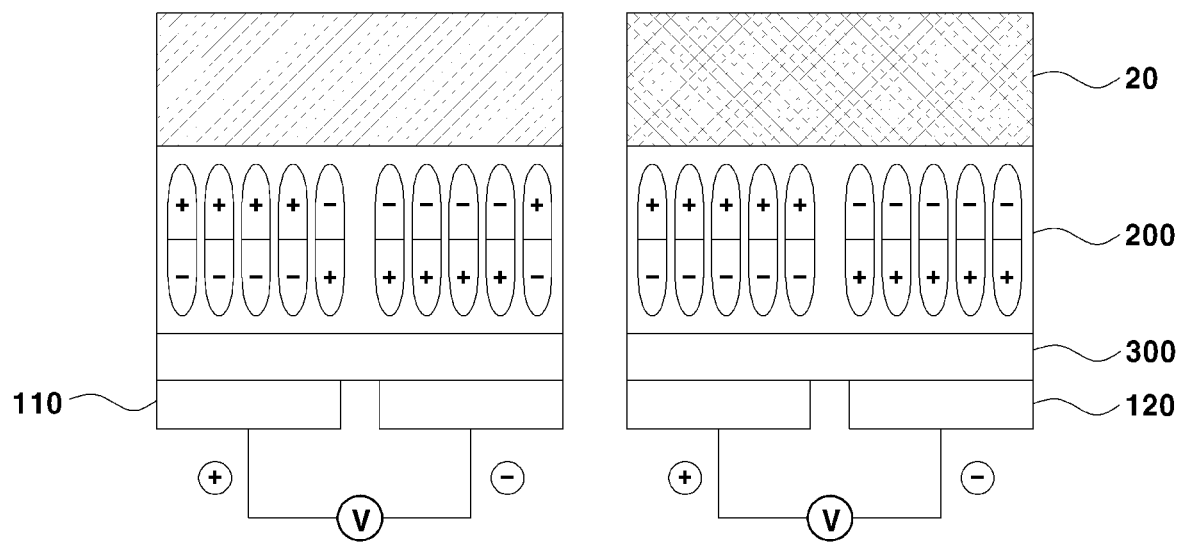
FIG. 7A to FIG. 7F are diagrams illustrating driving methods of the liquid detection sensors according to another embodiment.
Figure 7B:
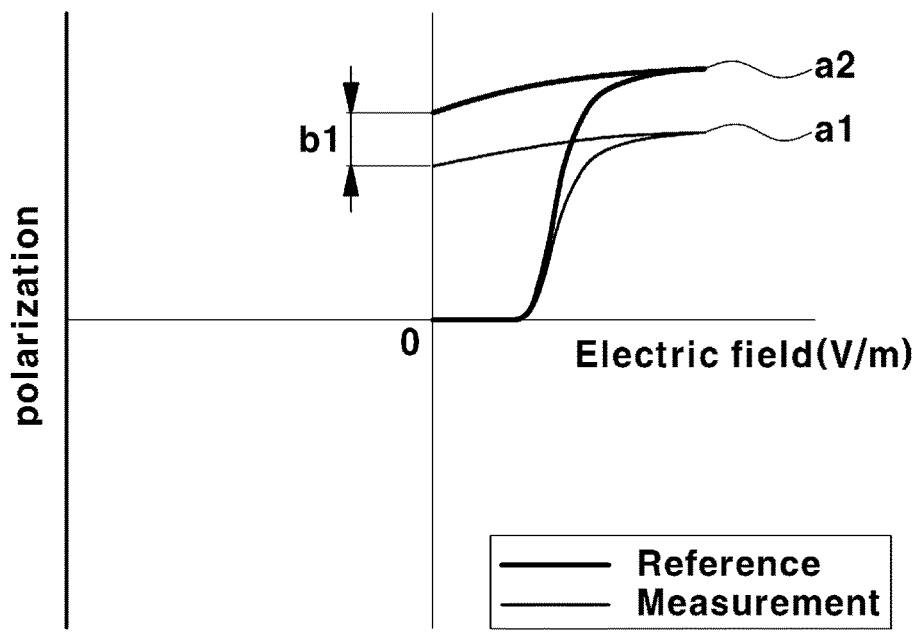

Referring to FIGS. 7A and 7B, a writing step according to one embodiment can provide a target liquid 20 on a receiving region 210 and can provide a direct current signal between the first electrode 110 and the second electrode 120 to generate a polarization in the ferroelectric layer 200. The left view of FIG. 7A is a diagram illustrating polarization of the ferroelectric layer 200 in an experimental example in which the target liquid 20 was provided on the receiving region 210, and the right view is a diagram illustrating polarization of the ferroelectric layer 200 in a comparative example in which the conductor is provided to the receiving region 210. The conductor can be a floated conductive layer. In the above experimental example, it can be observed that the polarization of the ferroelectric layer 200 can be smaller than the polarization of the ferroelectric layer 200 of the comparative example due to the polarity of the target liquid 20. In one embodiment, the magnitude of the voltage of the DC signal can be in the range of 0.5 kV to 5 kV.

FIG. 7B is a graph showing polarization according to an electric field applied to a liquid detection sensor. The first curve a1 is a graph showing the polarization of the experimental example, and the second curve a2 is a graph showing the polarization of the comparative example. As a result of comparing the residual polarization which is the polarization of the point where the magnitude of the electric field is 0 V/m, it can be seen that the magnitude of the residual polarization of the second curve a2 is larger than the magnitude of the residual polarization of the first curve a1. Information on the polarity of the target liquid 20 can be stored by the difference b1 between the residual polarization of the second curve a2 and the first curve a1.

Figure 7C:
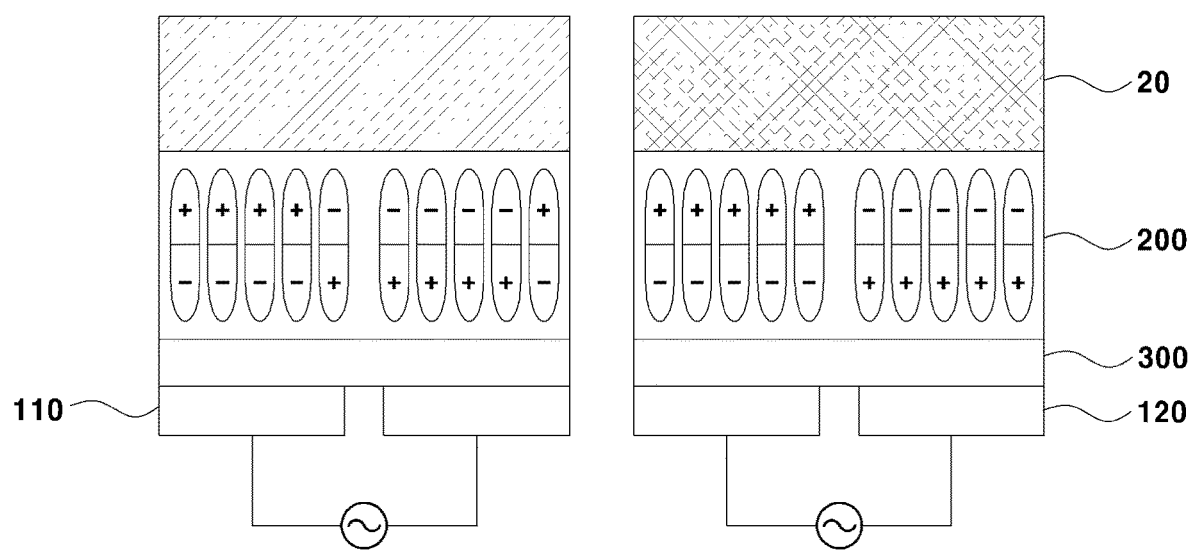
Figure 7D:
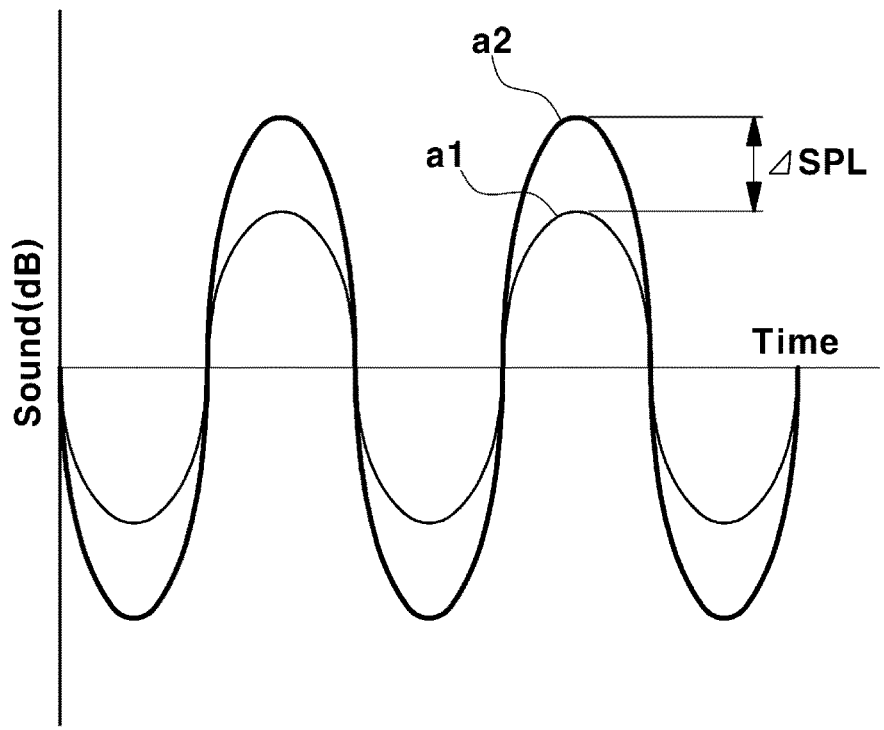

Referring to FIGS. 7C and 7D, a reading step according to an embodiment can replace a target liquid 20 with a conductive material and apply an AC signal between the first electrode 110 and the second electrode 120 to generate sound waves. The left diagram of FIG. 7C shows the polarization of the ferroelectric layer 200 in the experimental example providing a conductor on the receiving region 210, and the right diagram shows the polarization of the ferroelectric layer 200 in the comparative example providing the conductor on the receiving region 210.

FIG. 7D is a graph showing the strength of sound waves over time. The first curve a1 is a graph showing the intensity of the sound wave of the above experimental example, and the second curve a2 is a graph showing the intensity of the sound wave of the comparative example. It can be seen that the intensity of the sound waves of the second curve a2 is greater than that of the sound waves of the first curve a1. In one embodiment, in connection with the liquid information sensors 10a to 10f, the information indicating that the polarity of the target liquid 20 becomes greater as the difference between the intensities of the sound waves of the first curve a1 and the second curve a2 is getting larger can be obtained.

Figure 7E:
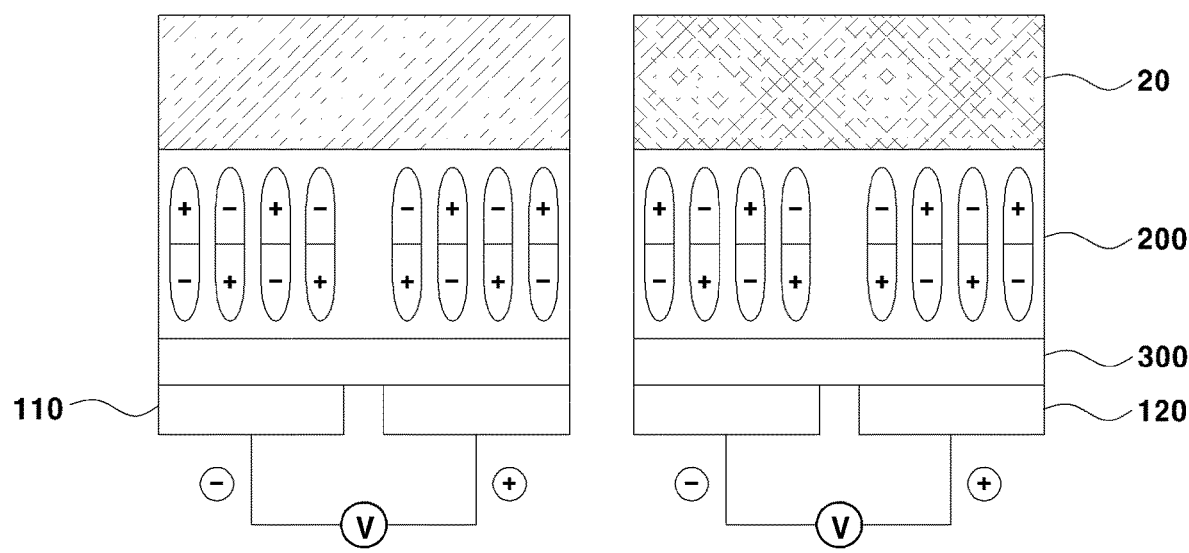
Figure 7F:
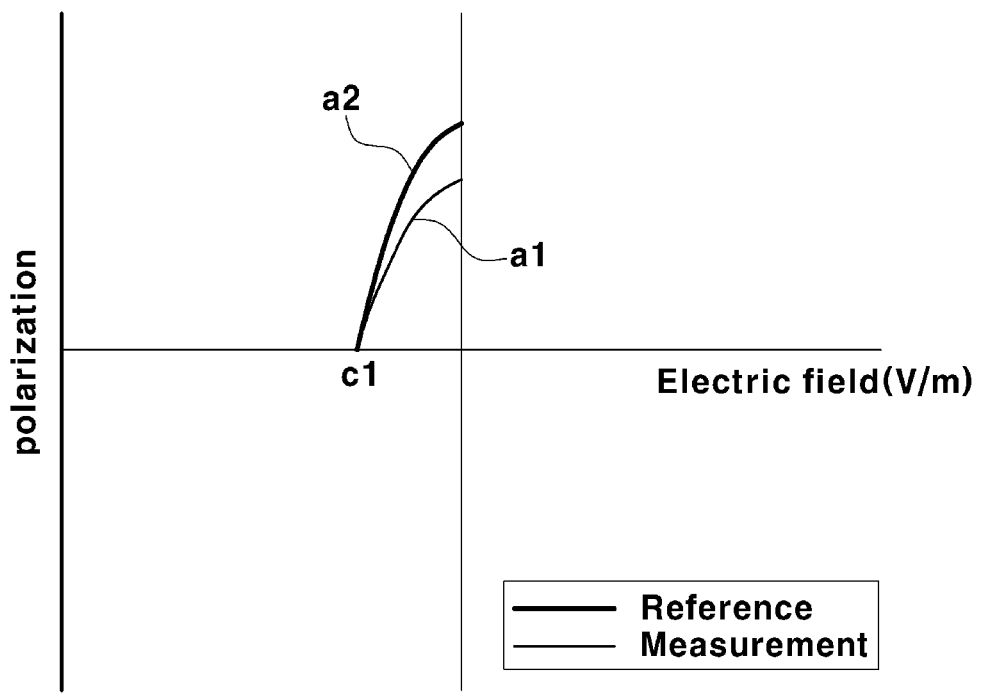

Referring to FIG. 7E and FIG. 7F, in the erasing step according to an embodiment, the polarization can be removed by applying a DC signal having a polarity opposite to the direct current signal of the writing step between the first electrode 110 and the second electrode 120. The left diagram of FIG. 7E shows the polarization of the ferroelectric layer 200 in the experimental example providing a conductor on the receiving region 210, and the right diagram shows a comparative example providing a conductor on the receiving region 210. The polarization of the ferroelectric layer 200 is shown. Depending on the DC signal of the opposite polarity, an electric field of more than a coercive field, which is the size of an electric field capable of erasing existing residual polarization can be applied to the ferroelectric layer 200. Accordingly, it can be seen that the residual polarization is erased in the above experimental example and the comparative example.

FIG. 7F is a graph showing polarization according to an electric field applied to a liquid detection sensor. The first curve a1 is a graph showing the polarization of the experimental example, and the second curve a2 is a graph showing the polarization of the comparative example. In one embodiment, it can be seen that the difference between the residual polarization of the first curve a1 and the second curve a2 at a point c1 where the electric field of more than the coercive field size is applied becomes 0 μC/cm2. Accordingly, after erasing the residual polarization, reusable liquid information sensors 10a to 10f can be provided to collect information of another target liquid 20.

According to an embodiment of the present invention, the intensity of the sound wave which varies according to the residual polarization formed in the ferroelectric layer 200 can be measured in the writing step. Therefore, even if the target liquid 20 is partially vaporized, it is possible to collect the information of the target liquid 20. Consequently, the limitation of measurement time can be relaxed, and the reliability and accuracy of the liquid information sensors 10a to 10f can be improved remarkably. In addition, it is possible to implement a sensor having a memory function by storing the information for a predetermined time. Accordingly, the liquid information sensors 10a to 10f can be applied to biomedical diagnostics, detection of harmful liquids in humans, cell number screening using microfluidics, or cell classification. Alternatively, a nonvolatile touch pad using sound waves can be implemented.

While the present disclosure has been described with reference to the embodiments illustrated in the figures, the embodiments are merely examples, and it will be understood by those skilled in the art that various changes in form and other embodiments equivalent thereto can be performed. Therefore, the technical scope of the disclosure is defined by the technical idea of the appended claims The drawings and the forgoing description gave examples of the present invention. The scope of the present invention, however, is by no means limited by these specific examples. Numerous variations, whether explicitly given in the specification or not, such as differences in structure, dimension, and use of material, are possible. The scope of the invention is at least as broad as given by the following claims.

What is claimed is:

1. A liquid information sensor for collecting information of a target liquid comprising, at least more than one electrode set wherein each electrode set includes a first electrode, and a second electrode which is disposed spaced apart from the first electrode and to which an alternating current signal is applied between the first electrode and the second electrode; and a ferroelectric layer including a first side and a second side facing each other, wherein the first electrode and the second electrode are formed on the first side, a receiving region for receiving the target liquid is defined on the second side, and sound waves are generated by physical vibration when the AC signal is applied, wherein a first portion of the ferroelectric layer is disposed between the first electrode and the target liquid, a second portion of the ferroelectric layer is disposed between the second electrode and the target liquid, and the first portion is apart from the second portion, and wherein the liquid information sensor is configured to collect a piece of information of the target liquid from a change in intensity of the sound wave that varies according to a magnitude of a polarity of the target liquid, and the intensity of the sound wave is changed according to a magnitude of a relative dielectric constant of the target liquid.

2. The liquid information sensor of the claim 1, wherein the intensity of the sound wave increases as the magnitude of the polarity of the target liquid increases.

3. The liquid information sensor of the claim 1, wherein the intensity of the sound wave is linearly proportional to the relative dielectric constant of the target liquid.

4. The liquid information sensor of the claim 1, wherein a frequency of the AC signal is in the range of 20 Hz to 20 kHz.

5. The liquid information sensor of the claim 1, wherein the intensity of the sound wave increases as a frequency of the AC signal increases.

6. The liquid information sensor of the claim 1, wherein the ferroelectric layer includes PVDF, P(VDF-TrFE), P(VDF-CTFE), P(VDF-CFE), P(VDFHFP), P(VDF-TrFE-CTFE), P(VDF-TrFE-CFE), P(VDF-TrFE-HFP) or a combination thereof.

7. The liquid information sensor of the claim 1, further comprising a protection layer which is disposed between the first electrode and the first side of the ferroelectric layer and between the second electrode and the first side of the ferroelectric layer, and which when the AC(alternating current) signal is applied, prevents a short circuit generated due to a ferroelectric layer between the first electrode and the second electrode.

8. The liquid information sensor of the claim 7, wherein the protection layer is a conductive polymer.

9. The liquid information sensor of the claim 1, further comprising a microphone for measuring the intensity of the sound wave.

10. The liquid information sensor of the claim 1, further comprising a cover formed on the ferroelectric layer to prevent vaporization of the target liquid.

11. The liquid information sensor of the claim 1, wherein the electrode set is a plurality of electrode sets arranged in an array.

12. The liquid information sensor of the claim 1 is a tubular sensor formed by rolling a laminate of the electrode set and the ferroelectric layer.

13. The liquid information sensor of the claim 12, wherein a radius of curvature of the tubular sensor is in the range of 1 mm to 100 mm.

14. The liquid information sensor of the claim 1, wherein the electrode set is a plurality of electrode sets spaced apart from each other by a predetermined distance.

15. A method of driving a liquid information sensor for collecting information of a target liquid, the method comprising,
- providing a target liquid to the receiving region;
- generating a sound wave by applying an alternating current signal between a first electrode and a second electrode; and
- measuring an intensity of the sound wave that varies according to a magnitude of a polarity of the target liquid, where the intensity of the sound wave is changed according to a magnitude of a relative dielectric constant of the target liquid,
- wherein the liquid information sensor comprises,
  - at least more than one electrode set wherein each electrode set includes a first electrode, and a second electrode which is disposed spaced apart from the first electrode and to which an alternating current signal is applied between the first electrode and the second electrode; and
  - a ferroelectric layer including a first side in contact with the first electrode and the second electrode and a second side facing the first side and defining a receiving region for receiving the target liquid, and generating sound waves by physical vibration when the AC signal is applied,
  - wherein a first portion of the ferroelectric layer is disposed between the first electrode and the target liquid, a second portion of the ferroelectric layer is disposed between the second electrode and the target liquid, and the first portion is apart from the second portion.

16. The method of driving a liquid information sensor of the claim 15,
- wherein the target liquid is provided continuously, and the intensity of the sound wave is measured according to in-situ method,
- wherein, in the in-situ method, while the target liquid is continuously provided, the intensity of sound wave generated by the liquid information sensor is continuously measured to measure a change in the sound wave over time.

17. A method of driving a liquid information sensor for collecting information of a target liquid, the method comprising,
- a writing step for providing the target liquid on the receiving region and for applying a direct current signal between the first electrode and the second electrode to generate polarization in the ferroelectric layer;
- a reading step for replacing the target liquid with a conductive material and for generating sound waves by applying an alternating current signal between the first electrode and the second electrode, wherein an intensity of the sound wave is measured in the reading step, the measured intensity of the sound wave is compared with a reference intensity to estimate a magnitude of a polarity of the target liquid, and the intensity of the sound wave is changed according to a magnitude of a relative dielectric constant of the target liquid; and
- an erasing step for removing the polarization by applying a direct current signal having a polarity opposite to that of the direct current signal between the first electrode and the second electrode,
- wherein the liquid information sensor comprises,
  - at least more than one electrode set wherein each electrode set includes a first electrode, and a second electrode which is disposed spaced apart from the first electrode and to which an alternating current signal is applied between the first electrode and the second electrode; and
  - a ferroelectric layer including a receiving region in contact with the electrode set on one side and receiving the target liquid on the other side facing the one side, and generating sound waves by physical vibration when the AC signal is applied,
  - wherein a first portion of the ferroelectric layer is disposed between the first electrode and the target liquid, a second portion of the ferroelectric layer is disposed between the second electrode and the target liquid, and the first portion is apart from the second portion.

18. The method of driving a liquid information sensor of the claim 17, wherein a magnitude of the DC signal is in a range of 0.5 kV to 5 kV.

* * * * *